United States Patent [19]

Citri

[11] Patent Number: 5,091,306
[45] Date of Patent: Feb. 25, 1992

[54] METHOD AND KIT FOR TESTING FOR THE PRESENCE OF CATALASE IN MILK

[75] Inventor: Nathan Citri, Jerusalem, Israel

[73] Assignee: Yissum Research Development Company of the Hebrew University of Jerusalem, Jerusalem, Israel

[21] Appl. No.: 163,390

[22] Filed: Mar. 2, 1988

[30] Foreign Application Priority Data

Mar. 8, 1987 [IL] Israel .................................. 81822

[51] Int. Cl.$^5$ .............................................. C12Q 1/30
[52] U.S. Cl. ......................................... 435/27; 435/29; 435/259; 435/810; 436/23
[58] Field of Search ...................... 435/23, 24, 27, 259, 435/810, 219, 222, 29; 436/20, 22

[56] References Cited

U.S. PATENT DOCUMENTS

| | | | |
|---|---|---|---|
| 3,426,732 | 12/1975 | Rosen et al. | 435/27 |
| 4,065,357 | 12/1977 | Grover | 435/27 |
| 4,481,294 | 11/1984 | Downs | 435/259 |

FOREIGN PATENT DOCUMENTS

| | | | |
|---|---|---|---|
| 0078556 | 5/1983 | European Pat. Off. | 435/259 |
| 0145233 | 6/1985 | European Pat. Off. | |
| 0184260 | 6/1986 | European Pat. Off. | |
| 36496 | 11/1974 | Israel . | |
| 2065689 | 7/1981 | United Kingdom . | |

OTHER PUBLICATIONS

Bergmeyer, Methods of Enzymatic Analysis, vol. II, pp. 70–73 (1983).
Bergmeyer, H., Methods of Enzymatic Analysis, vol. II, pp. 126 and 165–166, (1983).
Daniels, F., et al., Physical Chemistry, 3rd Edition, (John Wiley & Sons, pubisher, New York), pp. 141, (1967).
Roger Grant, Claire Grant, Grant & Hackh's Chemistry Dictionary, 5th Edition, 1987, p. 118.

Primary Examiner—Esther L. Kepplinger
Assistant Examiner—Carol E. Bidwell
Attorney, Agent, or Firm—Darby & Darby

[57] ABSTRACT

The invention provides a method for testing for the presence of catalase in a milk sample comprising combining a milk sample with a substantially catalase-free alkaline protease enzyme enriched detergent to disrupt catalase containing somatic cells present therein and release active catalase therefrom in the present of a pH buffering salt having a concentration of at least 20 mM in the resulting sample solution and providing the solution with a pH in a range of about 7.0–8.0 and thereafter testing the sample for the presence of catalase, as well as providing a test kit for detecting the presence of catalase in milk comprising a substantially catalase-free alkaline protease enzyme enriched detergent and 20 to 400 micromoles of a pH buffer alone or in combination with any other solute capable of reducing the solubility of oxygen in milk and of providing the resulting milk solution with a pH in the range of about 7.0–8.0.

8 Claims, No Drawings

METHOD AND KIT FOR TESTING FOR THE PRESENCE OF CATALASE IN MILK

The present invention relates to a method for testing for the presence of catalase in a milk sample More particularly the present invention provides a highly sensitive method and test kit for rapid detection of catalase in a milk sample produced from mastitic udders.

As is known, bovine mastitis is by far the most important disease of dairy cows in terms of its frequency and economic importance.

In Israel Patent 36 496 published June 1974. there is described and claimed a method for testing for the presence of organic cells in a liquid which comprises the steps of disrupting said cells in a sample of the liquid by the combined action of a protease and detergent compatible therewith, whereby undegraded desoxyribonucleic acid (DNA) and active enzymes are released, and thereafter testing said sample for the presence of DNA and/or of a released enzyme.

In preferred embodiments of said patent said liquid is milk and said cells are somatic cells, and the released enzyme tested is catalase.

The test in said patent is based on the known principle that milk from mastitic udders contains leukocytes in large numbers, exceeding $10^5$ cells/ml. Disruption of leukocytes releases DNA and intracellular enzymes, e.g. catalase, which are normally undetectable in healthy milk. If the disruption of the leukocytes is carried out by the combined action of a protease and a detergent compatible therewith, the DNA is not degraded and the released enzymes are not inactivated within the test period. The released DNA can accordingly be readily detected through increase in the viscosity of the milk sample. Alternatively in addition, the released enzymes can be detected by a suitable test system. A particularly suitable test is the formation of bubbles by reaction of the released enzyme with hydrogen peroxide.

The combination of a protease (e.g. subtilisin) and a detergent compatible therewith constitutes a stable and effective disrupting preparation which causes rapid release of intact macromolecules and does not degrade DNA.

The basic principle of the present test is similar to that described in said patent. In this test, the assay of catalase activity follows treatment of the specimen with a cell disrupting preparation. The treatment is intended to remove possible accessibility barriers between catalase present inside the cells and its substrate. The presence of such barriers will slow down the catalytic reaction and thus interfere with the detection of catalase. Disruption of cells is thus intended for making the total catalase content of the specimen instantly detectable.

As described and explained in said patent, although disruption of somatic cells can be accomplished by several well-known procedures, none of these is acceptable for the present purpose. The available methods are usually laborious and time-consuming, or else not generally effective. The most reliable methods of disruption depend on the use of expensive equipment (e.g. mechanical, sonic or ultrasonic disintegrators).

By using the method of the present invention the need for incubation is completely obviated and thus the difficulties involved are eliminated. The test as described below is simple, rapid and direct. It requires no preparation, skill or equipment, and can be carried out on the farm and even as a "cow-side" test.

The addition of the protease and detergent to a sample of milk causes maximal exposure of intracellular enzymes present in that sample within 3 minutes at room temperature.

The protease detergent disrupting agent acts rapidly under Physiological conditions of pH and temperature, and does not interfere with the detection of the catalase released by the treatment.

Initial studies summarized in said patent, have confirmed that disruption increases the sensitivity of catalase detection to the Point where it can be used for rapid screening for Mastitis. In subsequent field tests it became apparent, however, that the preferred embodiment, namely impregnated swabs, exemplified in said patent (Example 2) did not yield consistent results.

In the test described in said patent (Example 2) positive scores were recorded for milk samples containing $0.8-3.4 \times 10^5$ cells per ml., whereas a negative reaction was recorded for a milk sample containing no leukocytes. In subsequent field tests it was found however, that most samples encountered contain some somatic cells and therefore will not yield a negative reaction, even if mastitis is not present. The diagnostic value of the test must then depend on a clear cut distinction between a significant and an insignificant level of catalase activity. The test, as described in the above document could not provide that distinction. Furthermore, it also became clear, following a careful and detailed study of said patent, that there were no clues in said patent document that would help in tracing the roots of the problem or suggest a solution. Therefore, said method and said patent were abandoned.

Only ten years later was said method once again considered, however, since said patent provided no clues as to an obvious remedy to the problem which resulted in the original abandonment thereof, further research was necessary and directed to the design of a modified method and test kit which would yield unambiguous results. The specific aims of the subsequent research were:

(a) Increase of sensitivity, so as to ensure clear response of positive specimens
(b) Elimination of irrelevant positive-characterizing foamformation, so as to avoid spurious responses in negative specimens.

A large series of potentially useful combinations of proteases and compatible detergents was investigated. These included both ready-made commercial preparations and experimental combinations of technical grade enzyme preparations and detergents. It turned out that the requirement for an effective cell disrupting preparation imposed severe limitations on the choice of reagents. Laboratory made Preparations were invariably inferior to the commercial preparations, mainly for reasons of enzyme-detergent incompatability.

As a result of said extensive research there has been found and there is now provided according to the present invention a method for testing for the presence of catalase in a milk sample comprising combining said milk sample with a substantially catalase-free alkaline protease enzyme enriched detergent to disrupt catalase containing bacterial and somatic cells present therein and release active catalase therefrom in the presence of a pH buffering salt having a concentration of at least 20 mM in the resulting sample solution and providing said solution with a pH in a range of about 7.0–8.0 and thereafter testing said sample for the presence of catalase.

In the preferred embodiments of the present invention said catalase is detected by the addition of $H_2O_2$ whereby foam generating $O_2$ is released into said solution, and the method is preferably carried out by adding other solutes to said solution in addition to said buffer whereby said buffer and said additional solute decrease the solubility of oxygen released into said solution thereby increasing foam generation.

Preferably said buffer is a solution of phosphate buffer pH 7.0–8.0 and is provided at a concentration of between 20 to 50 mM, sufficient to decrease the solubility of oxygen in the milk.

Thus the present invention also provides a test kit for detecting the presence of catalase in milk comprising a substantially catalase free alkaline protease enzyme enriched detergent and 20 to 400 micromoles of a pH buffer alone or in combination with any other solute capable of reducing the solubility of oxygen in milk and of providing the resulting milk solution with a pH in the range of about 7.0–8.0.

In U.S. Pat. No. 3,926,732 there is disclosed a method of assaying a milk comprising the addition of galactose oxyidase enzyme and a leuko dye to indicate mastitis. In U.S. Pat. No. 3,764,479 there is disclosed a filter paper disk containing acetylcholine, sodium bicarbonate and sodium carbonate buffer. The disk further includes a catalase enzyme and hydrogen peroxide. Furthermore, in U.S. Pat. No. 4,065,357 there is disclosed the use of hydrogen peroxide in a method of detecting catalase.

None of said patents, however, teach or suggest the method and kit of the present invention for rapid detection of catalase in a milk sample produced from mastitic udders.

Several highly soluble inorganic salts (e.g. ammonium sulfate, sodium-, potassium-, magnesium-chlorides etc.) as well as soluble organic compounds (e.g. urea, sucrose etc.) or buffers can be used as said additional solute at sufficiently high concentrations to expell dissolved oxygen instead of, or in addition to said buffers.

Thus it has been discovered that contrary to the teachings of said patent it is not sufficient to utilize the cell disrupting activity of a protease and a detergent compatible therewith and that even the preferred enzyme enriched washing powder marketed under the name BIOOR ® by Shemen Ltd. Haifa Israel, exemplified in said Patent in fact does not give satisfactory results.

Instead there must be selected and used a substantially catalasefree alkaline protease enzyme enriched detergent and only the enzyme enriched washing powder marketed under the name BIOMAT ® by Witco Chemical Ltd. P.O. Box 975, Haifa Israel has so far been found to fill this criterion.

Further it has now been found that 0.01 M phosphate, as taught in the examples of said patent, is inadequate for reducing the solubility of oxygen in the sample. Furthermore, since at least twice as much and preferably even more than 5 times as much buffer is added alone or in combination with any other solute capable of reducing the solubility of oxygen in milk, then the sensitivity of the test is increased even more due to the fact that all oxygen generated by the catalase reaction enters into the foam generating process.

Furthermore, it has now been found that the use of impregnated swabs precludes the use of a well defined visual cut-off point allowing an unambiguous distinction between healthy and suspect milk samples derived from subclinical cases of mastitis. In the present test, the reagents are dispensed in a soluble or dissolved form. Thus, no solid element is introduced into the milk sample and hence, nothing is present that may interfere with the direct visual scoring of the results.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

DETECTION OF MASTITIS

MATERIALS

Test Tubes, polystyrene. 7×11 mm, Nunc 3-40339

Hydrogen Peroxide (30%) from BDH Chemicals Ltd.

Amido Black (Aniline Blue Black) from Analco, Bethesda, Md.

BM powder (BIOMAT)* marketed by WITCO Chemical Ltd. POB 975, Haifa 31009

*(Enzyme-enriched washing powder. The enzyme is an alkaline protease Produced by a Carlsberg strain of *Bacillus subtilis* and marketed under the name of Alkalase or Subtilisin.)

REAGENTS

BMP: BM powder was ground with equal weight of $K_2HPO_4$ and stored at room temperature as a powder mix (BMP).

| Solvent: (mixed daily) | Phosphate buffer 1 M, pH | 7.3–5.0 ml |
|---|---|---|
| | Amido Black, 2 mg/ml | –2.0 ml |
| | Hydrogen Peroxide, 30% | –1.5 ml |
| | Distilled Water | –1.5 ml |

Reagent: (prepared daily) BMP (1.0 g) dissolved in 10 ml of above solvent mix.

PROCEDURE

1. Place milk (1.0) in test tube and add reagent (0.1 ml).
2. Mix contents by tapping bottom of tube, and place in rack for 3 min.
3. Record results as follows:
Ring of foam—Negative
Head of foam—Positive (Height of head proportional to level of catalase in sample.

COMMENTS:

The visual determination of the positive reaction is facilitated by:
  1. the detergent, which participates in the disruption of the cells, and is also suitable for providing a foam layer which forms when oxygen is released from hydrogen peroxide by the action of catalase; and 2. The dye (Amido Black) which provides a dark background against which the foaming (Positive reaction) is clearly visible.

The above formulation therefore satisfies the requirements for a rapid and reliable test for catalase in milk. Furthermore, the addition of both solid and dissolved phosphates serves a dual purpose. It acts as a buffer, so that all milk specimens are examined at the optimal pH. The dissolved salt also serves to decrease the solubility of the oxygen released by the catalase reaction and thus to enhance the sensitivity of the test.

The test was evaluated with milk samples collected at the Netiv Halamed Heh farm on November 11th, 1986. The samples were tested within 4 hours and retested after overnight storage at 4°. The results were identical in both tests. The following evaluation is based on comparing results with the present kit (BMP) and those obtained in parallel with the standard Californian Mastitis Test (CMT) which served as a reference system.

TABLE 1

| Total No. 93 | | % | |
|---|---|---|---|
| True positive | 23 | Sensitivity | 88.5 |
| False positive | 13 | Specificity | 80.6 |
| True negative | 54 | Positive pred value | 63.9 |
| False negative | 3 | Negative pred value | 94.7 |

EXAMPLE 2

DETECTION OF MASTITIS

All details were as in Example 1, except for the following:

1. The solvent was prepared on Dec. 16th, 1986 and stored in a dark bottle at room temperature. That preparation was subsequently used for all tests listed below.
2. The milk samples were collected as before on different days (see Table 2 below) and evaluated exactly as described in Example 1.

TABLE 2

| | SERIES I (Dec. 23, 1986) | SERIES II (December 28, 1986) | SERIES III (January 5, 1987) |
|---|---|---|---|
| Total No. | 110 | 56 | 106 |
| True positive | 10 | 3 | 34 |
| False positive | 19 | 2 | 12 |
| True Negative | 80 | 50 | 58 |
| False Negative | 1 | 1 | 2 |
| Sensitivity | 90.1% | 75.0% | 94.4% |
| Specifity | 80.0% | 96.2% | 82.9% |
| Pos. pred value | 34.5% | 60.0% | 73.9% |
| Neg. pred value | 98.8% | 98.0% | 96.7% |

EXAMPLE 3

COMPARISON OF PRESENT (BMP) AND STANDARD (CMT) KITS

All details are as in Example 2 except for the following:

1. The samples collected on Jan. 5th, 1987 and stored at 4° for 24 hours were now pooled so that each pooled sample contained equal volumes of 4 individual samples of the 4 quarters of an individual udder. Thus, each pooled sample now tested represented milk produced by each cow (rather than each quarter).

2. Each pooled sample was tested by the CMT and the present (BMP) method. The results are summarized in Table 3.

TABLE 3

| Pool (Positive*: Total) | CMT Positive | CMT Negative | BMP Positive** | BMP Negative |
|---|---|---|---|---|
| 0/4 | 0 | 9 | 0 | 9 |
| 1/4 | 2 | 6 | 8[3-4] | 0 |
| 2/4 | 4 | 0 | 4[5-7] | 0 |
| 3/4 | 6 | 0 | 6[>7] | 0 |

*Number of infected quarters as determined by CMT test before pooling
**Figure in brackets gives height (in mm) of foam head The method and test kit of the present invention thus also have the following advantages:

1. The buffered enzyme-detergent combination used here does not impair the catalase activity:
2. It is substantially catalase-free;
3. The solutes ensure proper buffering and the release of the product of the catalase reaction, oxygen, from the solution; and
4. The foam formed is stable for 1-2 hrs, or more, thus preventing escape of oxygen into the air.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A method for testing for the presence of catalase in a milk sample as an indication of the presence of somatic cells therein which comprises:

forming an aqueous solution of a substantially catalase-free alkaline protease-enriched detergent which is capable of foaming and hydrogen peroxide and further containing at least 20 mM of a pH buffer wherein the concentration of said buffer is sufficient to provide a pH in the range of 7.0-8.0 upon the addition of said milk sample to said solution;

adding said milk sample to said aqueous solution to form an admixture for a time and under conditions sufficient to allow the release of catalase from said somatic cells; and thereafter determining the presence of catalase in said milk sample by visually observing the extent of foam generated in said admixture, said buffer serving to increase the amount of released oxygen available to generate said foam.

2. A method according to claim 1 comprising adding another solute to said solution in addition to said buffer whereby said buffer and said additional solute decrease the solubility of oxygen released into said solution thereby increasing foam generation.

3. A method according to claim 1 wherein said buffer is a phosphate buffer.

4. A method according to claim 1 wherein said buffer is presents at a concentration of between 20 and 50 mM to decrease the solubility of oxygen in milk.

5. A method according to claim 1 wherein said protease is subtilisin.

6. A method according to claim 1 wherein said catalase-free alkaline protease detergent is in the form of a catalase free commercial enzyme-enriched washing powder.

7. A test kit for detecting the presence of catalase in milk as an indication of the presence of somatic cells therein comprising a substantially catalase-free alkaline protease enriched detergent which is capable of foaming and 20 to 400 micromoles of a pH buffer alone or in combination with any other solute capable of reducing the solubility of oxygen in milk and of providing the resulting milk solution with a pH in the range of about 7.0–8.0.

8. A testing medium for detecting the presence of catalase in a milk sample as an indication of the presence of somatic cells therein which comprises:

an aqueous solution containing a substantially catalase-free alkaline protease-enriched detergent which is capable of foaming, hydrogen peroxide, and 20–400 micromoles of a pH buffer alone or in combination with another solute capable of reducing the solubility of oxygen wherein the concentration of said buffer is sufficient to provide a pH in the range of 7.0–8.0 after admixture with a milk sample.

* * * * *